United States Patent
Olson (10) Patent No.: US 6,575,953 B2
(45) Date of Patent: Jun. 10, 2003

(54) ABSORBENT ARTICLES HAVING HINGED FASTENERS

(75) Inventor: Christopher Peter Olson, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 10/072,741

(22) Filed: Feb. 8, 2002

(65) Prior Publication Data

US 2002/0095131 A1 Jul. 18, 2002

Related U.S. Application Data

(63) Continuation of application No. 09/444,635, filed on Nov. 22, 1999, now Pat. No. 6,454,751.
(60) Provisional application No. 60/112,775, filed on Dec. 18, 1998.

(51) Int. Cl.$^7$ ................................................ A61F 13/15
(52) U.S. Cl. .................... 604/396; 604/386; 604/387; 604/390; 604/385.01
(58) Field of Search .................. 604/396, 386, 604/385.01, 385.24, 385.25, 387, 390

(56) References Cited

U.S. PATENT DOCUMENTS

| | | | |
|---|---|---|---|
| 2,957,512 A | 10/1960 | Wade et al. | |
| 3,277,547 A | 10/1966 | Billarant | |

(List continued on next page.)

FOREIGN PATENT DOCUMENTS

| | | |
|---|---|---|
| EP | 0 526 868 A2 | 2/1993 |
| EP | 0 528 282 A2 | 2/1993 |
| EP | 0 320 991 B | 5/1994 |
| EP | 0 487 921 B1 | 9/1995 |
| EP | 0 812 584 A2 | 12/1997 |
| EP | 0 945 110 A2 | 9/1999 |
| EP | 0 755 239 B1 | 12/1999 |
| EP | 0 800 379 B1 | 12/1999 |
| EP | 0 721 769 B1 | 5/2000 |
| EP | 0 721 770 B1 | 5/2000 |
| EP | 0 547 497 B2 | 7/2000 |
| EP | 0 765 148 B1 | 11/2000 |
| EP | 0 951 266 B1 | 3/2002 |
| EP | 0 994 689 B1 | 9/2002 |
| FR | 1375254 | 9/1963 |
| WO | WO 00/15069 A1 | 3/2000 |
| WO | WO 00/19950 A1 | 4/2000 |
| WO | WO 00/19951 | 4/2000 |
| WO | WO 00/20206 A1 | 4/2000 |
| WO | WO 00/20207 A1 | 4/2000 |
| WO | WO 00/23025 A1 | 4/2000 |
| WO | WO 00/27236 A1 | 5/2000 |
| WO | WO 00/27328 A1 | 5/2000 |
| WO | WO 00/27329 A1 | 5/2000 |
| WO | WO 00/30581 A1 | 6/2000 |

(List continued on next page.)

OTHER PUBLICATIONS

Advertisement from One Step Ahead® catalog, Late Winter 2000, cover pages and p. 26 referencing "Handy's Training Pants," and a photocopy of a package of Handy's Junior Training Pants as advertised therein.

*Primary Examiner*—Weilun Lo
*Assistant Examiner*—Jacqueline F Stephens
(74) *Attorney, Agent, or Firm*—Thomas M. Gage; H. Michael Kubicki (57) ABSTRACT

A disposable absorbent article has an absorbent chassis and a fastening system. The fastening system includes a pair of first fastening components disposed in one waist region and at least one second fastening component disposed in an opposite waist region. The first fastening components include at least one hinge area that transversely bisects the first fastening components, allowing the fasteners to bend in conformity with the movements of the wearer's body.

8 Claims, 4 Drawing Sheets

U.S. PATENT DOCUMENTS

| | | | |
|---|---|---|---|
| 3,316,139 | A | 4/1967 | Alford et al. |
| 3,319,307 | A | 5/1967 | Marforio |
| 3,577,607 | A | 5/1971 | Ikoma et al. |
| 3,694,867 | A | 10/1972 | Stumpf |
| 3,842,832 | A | 10/1974 | Wideman et al. |
| 3,943,981 | A | 3/1976 | De Brabander |
| 4,051,854 | A | 10/1977 | Aaron |
| 4,201,203 | A | 5/1980 | Applegate |
| 4,209,563 | A | 6/1980 | Sisson |
| 4,259,957 | A | 4/1981 | Sonenstein et al. |
| 4,338,938 | A | 7/1982 | Seavitt |
| 4,418,123 | A | 11/1983 | Bunnelle et al. |
| 4,446,189 | A | 5/1984 | Romanek |
| 4,496,360 | A | 1/1985 | Joffe et al. |
| 4,516,975 | A | 5/1985 | Mitchell |
| 4,623,339 | A | 11/1986 | Ciraldo et al. |
| 4,655,760 | A | 4/1987 | Morman et al. |
| 4,657,802 | A | 4/1987 | Morman |
| 4,701,170 | A * | 10/1987 | Wilson et al. ............... 604/385 |
| 4,705,710 | A | 11/1987 | Matsuda |
| 4,714,096 | A | 12/1987 | Guay |
| 4,718,901 | A | 1/1988 | Singheimer |
| 4,720,415 | A | 1/1988 | Vander Wielen et al. |
| 4,725,473 | A | 2/1988 | Van Gompel et al. |
| 4,789,699 | A | 12/1988 | Kieffer et al. |
| 4,834,742 | A * | 5/1989 | Wilson et al. ............... 604/389 |
| 4,847,134 | A | 7/1989 | Fahrenkrug et al. |
| 4,863,785 | A | 9/1989 | Berman et al. |
| 5,019,073 | A | 5/1991 | Roessler et al. |
| 5,087,253 | A * | 2/1992 | Cooper ................... 604/385.1 |
| 5,114,781 | A | 5/1992 | Morman |
| 5,116,662 | A | 5/1992 | Morman |
| 5,151,092 | A | 9/1992 | Buell et al. |
| 5,176,671 | A | 1/1993 | Roessler et al. |
| 5,185,052 | A | 2/1993 | Chappell et al. |
| 5,318,555 | A | 6/1994 | Siebers et al. |
| 5,383,872 | A | 1/1995 | Roessler et al. |
| 5,385,775 | A | 1/1995 | Wright |
| 5,407,439 | A | 4/1995 | Goulait |
| 5,451,219 | A | 9/1995 | Suzuki et al. |
| 5,503,908 | A | 4/1996 | Faass |
| 5,542,942 | A | 8/1996 | Kline et al. |
| 5,547,531 | A | 8/1996 | Allen et al. |
| 5,569,233 | A | 10/1996 | Goulait |
| 5,605,735 | A | 2/1997 | Zehner et al. |
| 5,611,791 | A | 3/1997 | Gorman et al. |
| 5,615,460 | A | 4/1997 | Weirich et al. |
| 5,624,427 | A | 4/1997 | Bergman et al. |
| 5,643,397 | A | 7/1997 | Gorman et al. |
| 5,647,864 | A | 7/1997 | Allen et al. |
| 5,669,900 | A | 9/1997 | Bullwinkel et al. |
| 5,681,302 | A | 10/1997 | Melbye et al. |
| 5,735,840 | A | 4/1998 | Kline et al. |
| 5,779,831 | A | 7/1998 | Schmitz |
| 5,814,178 | A | 9/1998 | Jacobs |
| 5,830,298 | A | 11/1998 | Jackson |
| 5,846,262 | A | 12/1998 | Sayama et al. |
| 5,888,607 | A | 3/1999 | Seth et al. |
| 5,891,547 | A | 4/1999 | Lawless |
| 5,897,547 | A | 4/1999 | Schmitz |
| 5,921,977 | A | 7/1999 | Schmitz |
| 5,925,027 | A | 7/1999 | Schmitz |
| 5,928,212 | A | 7/1999 | Kline et al. |
| 5,957,908 | A | 9/1999 | Kline et al. |
| 5,968,031 | A | 10/1999 | Schmitz |
| 5,997,981 | A | 12/1999 | McCormack et al. |
| 6,027,485 | A | 2/2000 | Matsushita et al. |
| 6,146,738 | A | 11/2000 | Tsuji et al. |
| D437,932 | S | 2/2001 | Ruman et al. |
| D437,933 | S | 2/2001 | Fletcher et al. |
| D438,614 | S | 3/2001 | Ratliff et al. |
| D439,662 | S | 3/2001 | Ratliff et al. |
| 6,230,374 | B1 | 5/2001 | Widlund |
| 6,264,643 | B1 | 7/2001 | Toyoda |
| 6,287,287 | B1 | 9/2001 | Elsberg |
| 6,302,871 | B1 | 10/2001 | Nakao et al. |
| 6,328,725 | B2 | 12/2001 | Fernfors |
| 6,329,016 | B1 | 12/2001 | Shepard et al. |
| 6,332,250 | B1 | 12/2001 | Igaue et al. |
| 6,352,528 | B1 | 3/2002 | Weber et al. |
| 6,447,497 | B1 | 9/2002 | Olson |
| 2002/0099353 | A1 | 7/2002 | |

FOREIGN PATENT DOCUMENTS

| | | | |
|---|---|---|---|
| WO | WO 00/30584 A1 | 6/2000 | |
| WO | WO 00/35395 A2 | 6/2000 | |
| WO | WO 00/35396 A1 | 6/2000 | |
| WO | WO 00/35398 A1 | 6/2000 | |
| WO | WO 00/35399 A1 | 6/2000 | |
| WO | WO 00/37009 A2 | 6/2000 | |
| WO | WO 00/37016 A1 | 6/2000 | |
| WO | WO 00/74621 A1 | 12/2000 | |
| WO | WO 01/88245 A2 | 11/2001 | Olson |

* cited by examiner

ABSORBENT ARTICLES HAVING HINGED FASTENERS

This application is a continuation of application Ser. No. 09/444,635 now U.S. Pat. No. 6,454,751 entitled Absorbent Articles Having Hinged Fasteners and filed in the U.S. Patent and Trademark Office on Nov. 22, 1999, which claims priority from U.S. Provisional Application No. 60/112,775 filed on Dec. 18, 1998. The entirety of application Ser. No. 09/444,635 is hereby incorporated by reference.

BACKGROUND OF THE INVENTION

The present invention relates to absorbent articles which are adapted to contain body exudates. More particularly, the invention pertains to pant-like disposable absorbent articles having hinged fastenings and methods of making such disposable absorbent articles.

Current disposable absorbent training pants for children going through the potty training stage have proved to be a particularly desirable and useful product. Such training pants generally include an absorbent chassis including a liquid impervious outer cover, a liquid pervious bodyside liner and an absorbent structure. The training pants further include elastic side panels that are joined to opposite side edges of the absorbent chassis. The chassis and side panels thereby form a unitary waist opening and two leg openings. Due principally to the elastic side panels, such training pants provide an exceptionally good fit to the wearer. Additional gathering means along the waist and leg openings may also be employed to further enhance fit.

Training pants are particularly suited for children who have outgrown, or believe they have outgrown, traditional diaper products. Children identify diaper products with babies, and most children do not like being identified with or as babies. Consequently, these children do not want to wear baby diapers, and instead prefer to wear training pants that look like adult underwear.

One drawback with current training pants, however, is that the interior of the pants cannot be occasionally checked for wetness without pulling the pant downward. This method of inspection can be problematic, for example, when the pant has been soiled. And while the integral side panels of current training pants are typically constructed to permit tearing in order to remove the pant, tearing the side panels is not suitable for simply inspecting the interior. Thus, it would be desirable to have a disposable absorbent article that provides the beneficial fit attributes of current training pants yet affords easier access to the interior of the pant for purposes of inspection.

SUMMARY OF THE INVENTION

In response to the above-referenced unfulfilled need in the prior art, a new disposable absorbent article and a method of making a disposable absorbent article have been discovered. The absorbent article has a pant-like appearance, which is desirable to children of toilet training age and is appealing to caregivers and to users of other ages. The absorbent article includes a fastening system that can be repeatedly fastened, unfastened and refastened. Despite the incorporation of a refastenable fastening system, the absorbent article provides the level of fit and comfort in use that has come to be associated with current training pants having elastic side panels. The fasteners of the absorbent article include "hinge areas" that, due to their location and design, cause the fasteners to bend in conformity with the movements of the wearer's body. The hinge areas prevent localized build up of stresses that would otherwise predispose the fastener to disengage unexpectedly.

In one embodiment, the present invention pertains to an absorbent article that defines a longitudinal axis and first and second longitudinally spaced waist regions. The absorbent article includes an absorbent chassis and a fastening system. The fastening system includes at least one first fastening component attached to the absorbent chassis and disposed in the first waist region and at least one second fastening component attached to the absorbent chassis and disposed in the second waist region. The first and second fastening components are adapted to releasably engage one another. The first fastening component has a length-to-width ratio of about 2 or greater and at least one hinge area that transversely bisects the first fastening component.

The first and second fastening components form a refastenable seam for securing the front and back waist regions together. If the training pant becomes soiled during use, the first fastening components can be disengaged from the second fastening components to easily remove the training pant from the waist of the wearer with reduced risk of undesirably soiling the clothes or legs of the wearer. The fastening components can also be easily disengaged from one another to inspect the training pant for possible soiling. Thus, the training pant is configured to be pulled on or off over the hips of the wearer such as conventional training pants and can be readily applied or removed by disengaging the fasteners similar to conventional diaper articles. Moreover, the first and second fastening components can be repositioned if necessary after the training pant has been pulled on over the legs and hips of the wearer.

A beneficial consequence of the hinged first fastening components is that the stiffness of the total length of the seam is reduced. This limits the amount of stress that can build up, which consequently reduces the likelihood that the fasteners will either buckle away from the body of the wearer or become partially disengaged from one another.

Advantageously, the location where the refastenable seam will bend during use can be controlled. Most desirably, the seam can be made to bend in areas that would otherwise give rise to fastener pop-opens. Additionally, the seam can be made to remain flat in the critical areas, such as for fit, leakage control or appearance. One common critical area is toward the lower portion of a longitudinally-oriented seam, near the leg opening of the garment. This critical area is at the maximum circumference of the body where the quadriceps insert into the hips. In this area, the side panels and chassis are under maximum stress and strain for two reasons. First, the maximum circumference puts the highest level of tension force into the elastic components of the side panels in this area of the pant. Second, the articulation of the leg also occurs in this area putting bending and compression forces into this area. This high tension and constant movement makes the lower portion of the reattachable seam prone to popping open.

The refastenable seams are formed when the first fastening components are engaged with the second fastening components. The refastenable seams are desirably relatively thin, narrow and flexible to afford the look and feel of a cloth garment. Thus, in particular embodiments, the refastenable seams have a length-to-width ratio of about 2 or greater, such as about 2 to about 25, particularly about 5 or greater, such as about 5 to about 8. The refastenable seams define a length dimension and a width dimension that is perpendicular to the length dimension. For a child of about 9 to about 15 kilograms (20–34 lbs.), for example, the length dimension is desirably from about 5 to about 13 centimeters, such as about 10 centimeters, and the width dimension is desirably from about 0.5 to about 3 centimeters, such as about 2 centimeters. Desirably although not necessarily, the length dimension is aligned generally parallel to the longitudinal axis of the absorbent article and the width dimension is aligned generally parallel to the transverse axis of the absorbent article. The term "generally parallel" as used herein refers to an angle within about 35 degrees or less of the referenced axis, and more particularly within about 20 degrees or less of the referenced axis.

In another embodiment, the present invention pertains to an absorbent article defining a longitudinal axis, first and second longitudinally spaced waist regions, and a crotch region which extends between and interconnects the first and second waist regions. The absorbent article includes an absorbent chassis and a fastening system, and the fastening system includes a pair of first fastening components attached to the absorbent chassis and disposed in the first waist region and at least one second fastening component attached to the absorbent chassis and disposed in the second waist region. The first and second fastening components are formed of mechanical fastening elements that are adapted to releasably engage one another. Moreover, each first fastening component has a length dimension, a width dimension, a length-to-width ratio of about 2 or greater, and at least one hinge area that transversely bisects the first fastening component.

The fastening components can comprise any refastenable fasteners suitable for absorbent articles, although desirably employing mechanical fastening elements rather than adhesive fastening elements. Suitable mechanical fastening elements can be provided by interlocking geometric shaped materials, such as hooks, loops, bulbs, mushrooms, arrowheads, balls on stems, male and female mating components, buckles, snaps, or the like. In particular embodiments, the fastening components comprise hook-and-loop fastening elements. One skilled in the art will recognize that the shape, density and polymer composition of the hooks and loops can be selected to obtain the desired level of securement between the fastening components and the mating fastening components. A more aggressive hook material can comprise a material with a greater average hook height, a greater percentage of directionally-aligned hooks, or a more aggressive hook shape.

The hinge areas can be formed in the fastening component material by cutting, scoring, perforating, melting such as with ultrasonics, cut and place spacing, or the like. Where a first fastening component is slit or segmented to form a hinge area, the spacing between the first fastening component segments should be kept to 15 millimeters or less, particularly 10 millimeters or less, more particularly 5 millimeter or less, and still more particularly 3 millimeters or less. The spacings create individual fastening component segments which jointly define the length and width dimensions of the fastening component.

The fastening components can include one, two, three, four or more hinge areas spaced along the length of the fastening components. Where increased flexibility of the fastening components is desired, each fastening component can even comprise 0.5 hinge areas per centimeter or more, particularly 1 hinge area per centimeter or more, more particularly 2 hinge areas per centimeter or more, such as 4 hinge areas per centimeter or more, where the number of hinge areas per centimeter is counted along the length dimension of the fastening component.

The hinge areas can be present anywhere along the length of the first fastening component. Desirably, the hinge areas are located along the length of the first fastening components where there is likely to be deformation and flexing during in use. One such area is often toward the inward end of the first fastening component, corresponding to the maximum circumference of the body where the quadriceps insert into the hips. In this area, the side panels and absorbent chassis are under maximum stress and strain. More particularly, the maximum circumference puts the highest level of tension into the side panels in this area of the pant. Also, the articulation of the leg occurs in this area thereby centering bending and compression forces in this area. This high tension and frequent movement makes the area of the refastenable seam particularly appropriate for location of the hinge areas.

Hence, in particular embodiments, each first fastening component defines an inner end edge disposed toward a leg opening of the absorbent article and an opposite outer end edge disposed toward a waist opening of the absorbent article, and at least one hinge area is offset along the length dimension of each fastening component so that it is closer to the inner end edge than the outer end edge. More particularly, the hinge area is desirably spaced from the inner end edge by about 5 to about 40 percent of the length of the fastener, particularly by about 5 to about 25 percent of the length of the fastener, and more particularly by about 5 to about 15 percent of the length of the fastener.

Thus another embodiment of the present invention pertains to a disposable absorbent pant defining a longitudinal axis, front and back longitudinally spaced waist regions, and a crotch region which extends between and interconnects the front and back waist regions. The pant includes a liquid permeable bodyside liner, a liquid impermeable outer cover bonded to the bodyside liner, and an absorbent assembly disposed between the bodyside liner and the outer cover. The pant also includes elastomeric side panels bonded to the outer cover in at least the back waist region. A pair of first fastening components are disposed on the elastomeric side panels in the back waist region, and a pair of second fastening components are disposed in the front waist region. The first and second fastening components comprise mechanical fastening elements that are adapted to releasably engage one another to define mating pairs of fasteners and form the waist and leg openings of the absorbent pant. Each of the first and second fastening components has an inner end edge disposed toward one of the leg openings, an opposite outer end edge disposed toward the waist opening, a length dimension that is generally parallel to the longitudinal axis, a width dimension, and a length-to-width ratio of about 5 or greater. At least one fastening component of each mating pair of fasteners has at least one hinge area that transversely bisects the at least one fastening component, and the hinge area is offset along the length dimension closer to the inner end edge than the outer end edge, that is, closer to the leg openings.

As noted above, the present fastening system prevents the localized build up of stresses that predispose the fastener to disengage unexpectedly. Fasteners lacking the disclosed hinge areas tend to experience areas of flexing and deformation creating concentrated stress areas. For mechanical-type fasteners, this problem is not adequately addressed by employing more aggressive fasteners, i.e., those creating higher peel strength, because such fasteners tend to be stiffer. Stiffer fastening material exacerbates rather than ameliorates the problem because stiffer materials increase the amount of stresses that build up when the fastener is flexed. Moreover, aggressive fasteners interfere with the additional objective of making the fastener easy to remove, particularly in the context of training pants where the user is a child.

The disclosed absorbent articles are adapted to be worn adjacent to the body of a wearer to absorb and contain various exudates discharged from the body. The absorbent articles are desirably pre-fastened to provide a pant-like product for the user. The product can then be pulled on like a conventional training pant, and subsequently checked or removed with the ease of a diaper-like product. Moreover, the product can be applied like a diaper rather than like a pant. Supplemental releasable fastening means such as frangible point bonds can be employed to maintain the absorbent article in a pant configuration until the user intentionally disengages the fasteners.

The fastening system allows for easy inspection of the interior of the pant-like product. If necessary, the fastening system also allows the pant to be removed quickly and easily. This is particularly beneficial when the pant contains messy excrement. If desired, the caregiver can completely remove the pant-like product and replace it with a new one without having to remove the child's shoes and clothing. The present fastening system can be used with a wide variety of absorbent products, including training pants, diapers, incontinence garments, or other garments using mechanical or adhesive fasteners.

The present invention also pertains to a method of making an absorbent article that defines a longitudinal axis, a transverse axis, a first waist region, an opposite second waist region, and a crotch region which extends between and interconnects the first and second waist regions. In one embodiment, a method of making an absorbent article comprises: providing an absorbent chassis; attaching at least one first fastening component to the absorbent chassis in the first waist region; and attaching at least one second fastening component to the absorbent chassis in the second waist region; wherein the first and second fastening components comprise mechanical fastening elements that are adapted to releasably engage one another and the first fastening component comprises at least one hinge area that transversely bisects the first fastening component.

A more detailed description of the construction and design of one form of training pant can be found in U.S. Pat. No. 4,940,464 issued Jul. 10, 1990 to Van Gompel et al., which is incorporated herein by reference. The Van Gompel et al. patent describes various materials of which the training pant can be made, and a method of constructing a training pant.

Definitions

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

Figure 2:
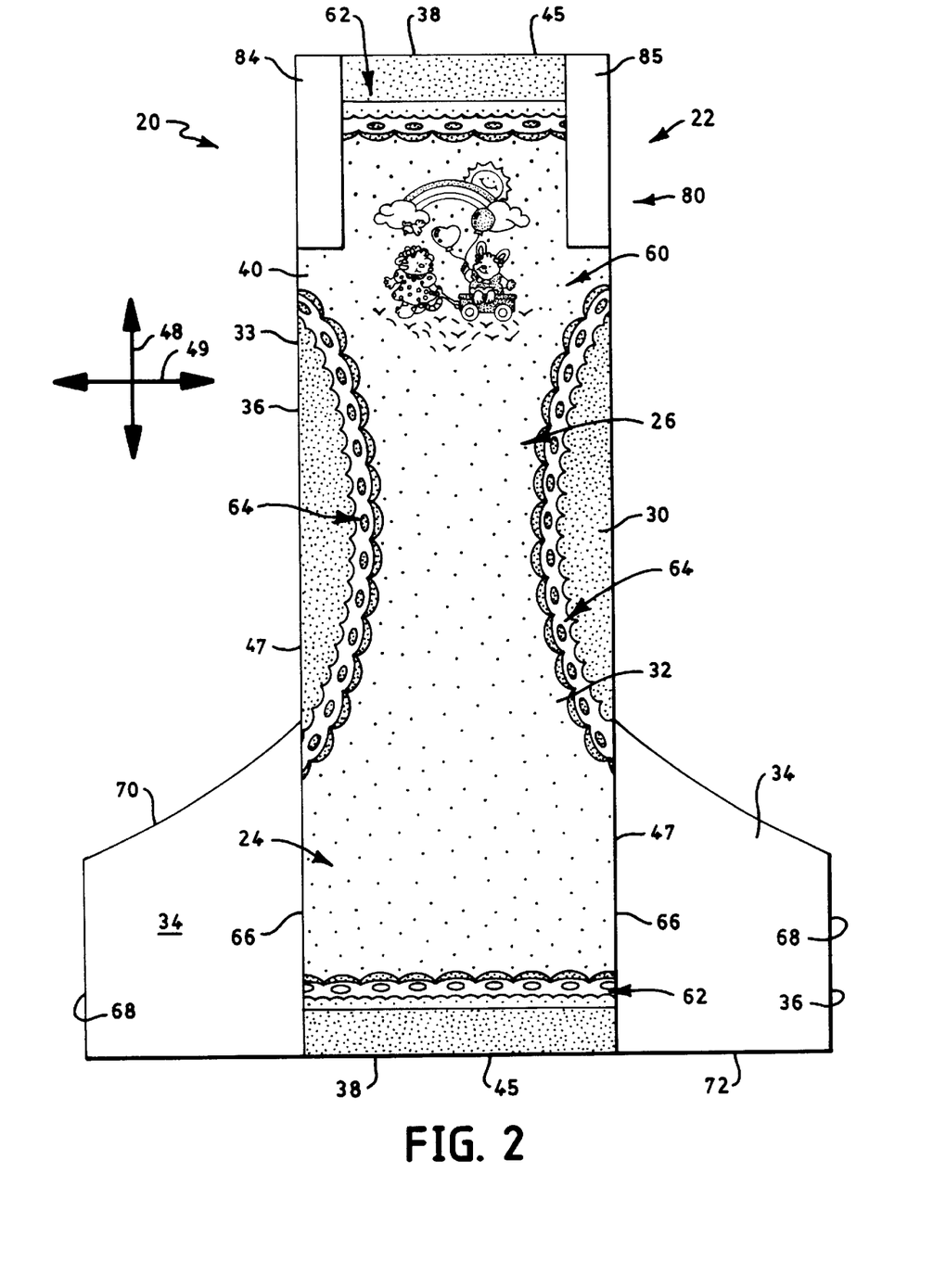
FIG. 2 illustrates a plan view of the disposable absorbent article shown in FIG. 1 in an unfastened, stretched and laid flat condition, and showing the surface of the article that faces away from the wearer.
Figure 3:
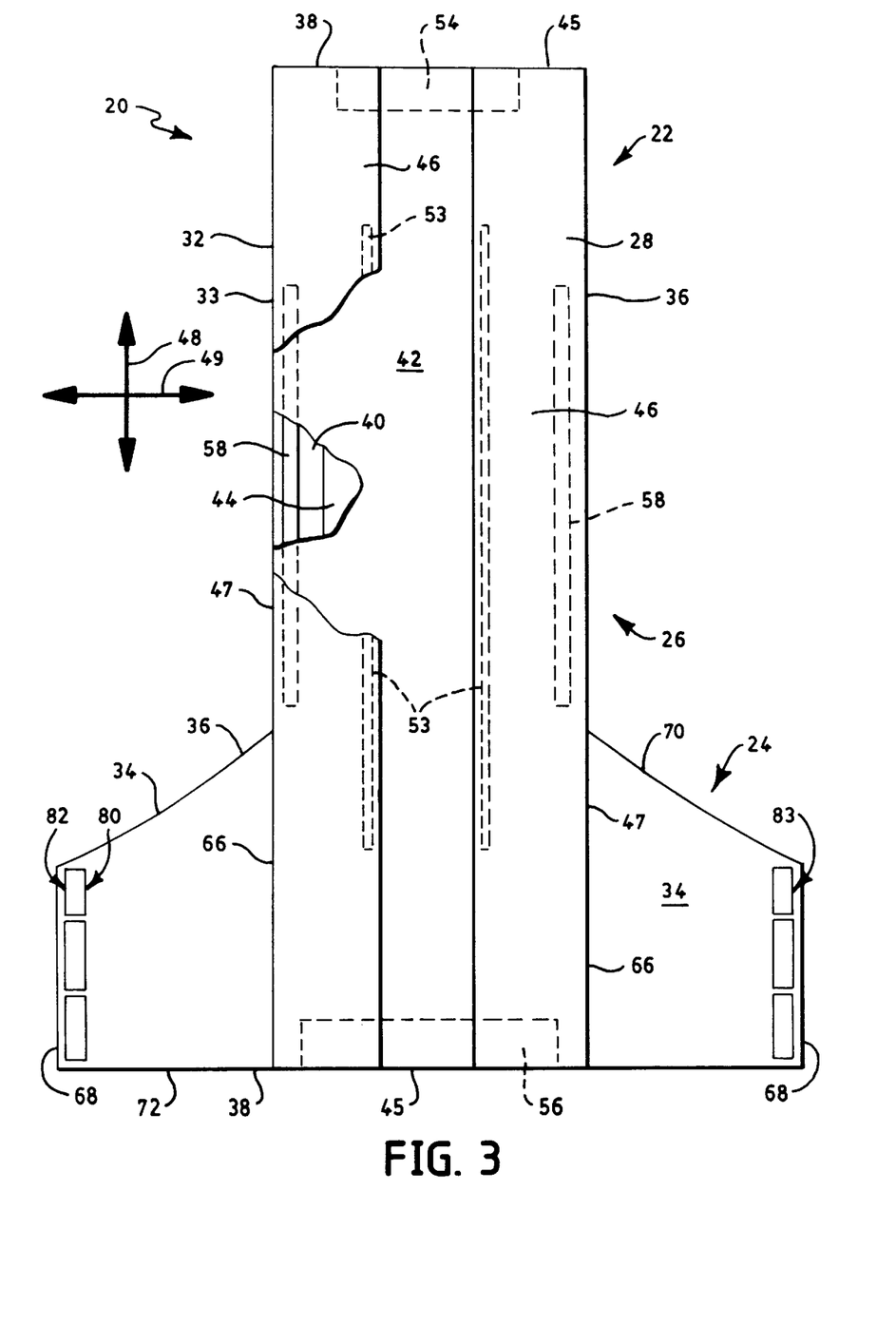
FIG. 3 illustrates a plan view similar to FIG. 2, but showing the surface of the article that faces the wearer when the article is worn, and with portions cut away to show the underlying features.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven web" means a web of material which is formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

"Transversely bisect" refers to a hinge or hinge area extending laterally across a fastening component so that the fastening component will bend in response to body movements about an axis that is generally perpendicular to the longitudinal axis of the fastening component.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The principles of the present invention can be incorporated into any suitable disposable absorbent article and its method of manufacture. Examples of such suitable articles include diapers, training pants, feminine hygiene products, incontinence products, other personal care or health care garments, or the like. For ease of explanation, the description hereafter will be in terms of a child's training pant.

Figure 1:
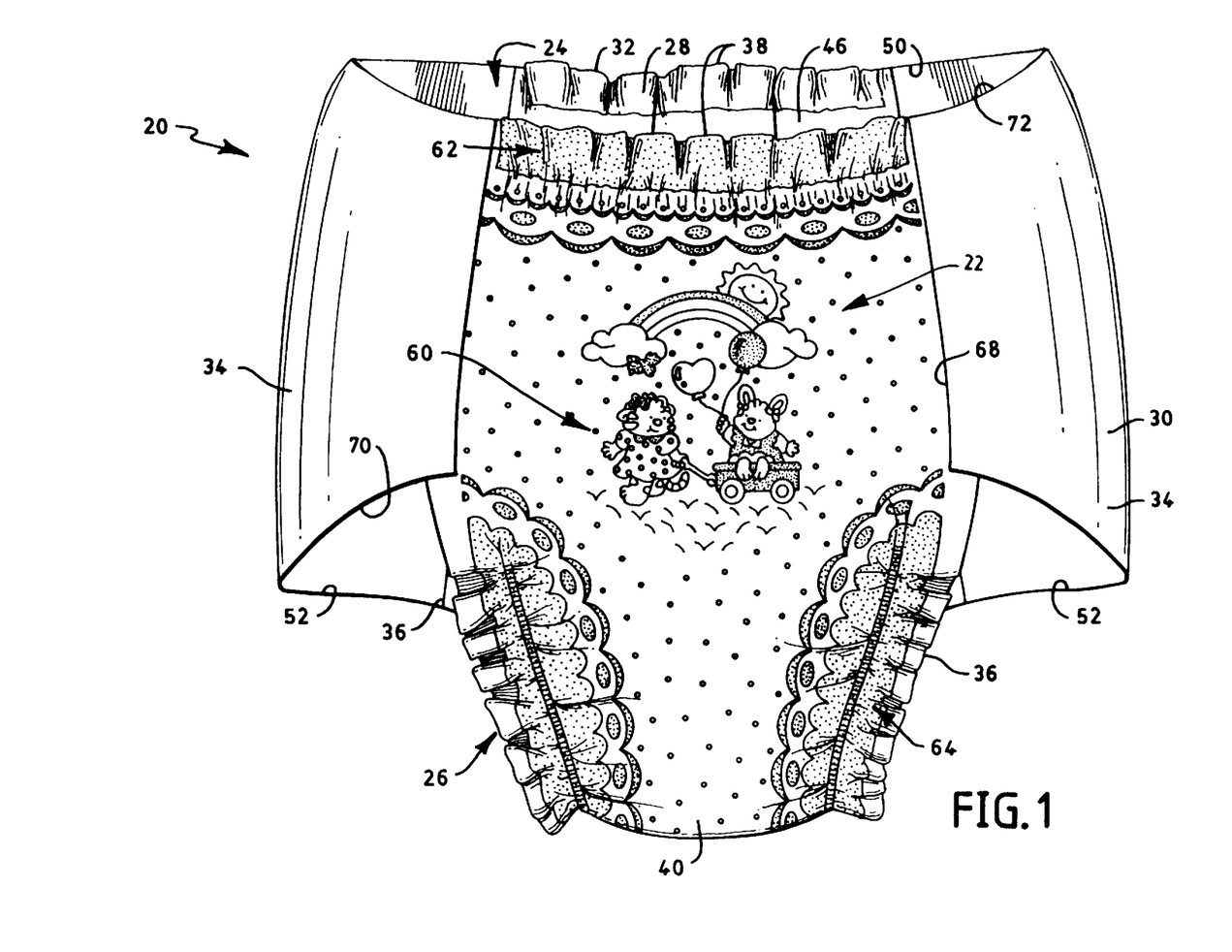
FIG. 1 illustrates a front perspective view of one type of disposable absorbent article incorporating the principles of the present invention.

With reference to FIG. 1, a disposable absorbent article, such as a training pant 20, is illustrated in a fastened condition as the product would be configured when worn. The training pant 20 comprises an absorbent chassis 32 and a fastening system 80. The absorbent chassis 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed side edges 36 and a pair of longitudinally opposed waist edges 38. The front waist region 22 is contiguous with the front waist edge 38, and the back waist region 24 is contiguous with the back waist edge 38.

The illustrated absorbent chassis 32 comprises a generally rectangular composite structure 33 and a pair of transversely opposed side panels 34. The composite structure 33 and side panels 34 may be integrally formed or comprise two or more separate elements, as shown. The illustrated composite structure 33 comprises an outer cover 40, a bodyside liner 42 which is connected to the outer cover in a superposed relation, an absorbent assembly 44 (FIGS. 2 and 3) which is located between the outer cover and the bodyside liner, and a pair of containment flaps 46 (FIGS. 1 and 3). The rectangular composite structure 33 has opposite linear end edges 45 that form portions of the front and back waist edges 38, and opposite linear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as illustrated in FIG. 1, the front and back waist regions 22 and 24 are joined together to define a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The side panels 34 comprise the portions of the training pant 20 which, when worn, are positioned on the side hip regions of the wearer. The waist edges 38 of the absorbent chassis 32 of the training pant 20 and the side panels 34 are configured to encircle the waist of the wearer when worn and provide the waist opening 50 which defines a waist perimeter dimension. The transversely opposed side edges 36 of the absorbent chassis 32 and the side panels 34 of the training pant 20 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes a front waist elastic member 54, a rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38, and can extend over part or all of the waist edges. The leg elastic members 58 are desirably operatively joined to the outer cover 40 and/or bodyside liner 42 along the opposite side edges 36 and positioned in the crotch region 26 of the training pant 20.

The flap elastic members 53, the waist elastics 54 and 56, and the leg elastics 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del., U.S.A.

The outer cover 40 desirably comprises a material that is substantially liquid impermeable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A. or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as liquid impermeable inner layer, or a single layer liquid impermeable outer cover 40, is a 1.0 mil polyethylene film commercially available from Edison Plastics Company of South Plainfield, N.J., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn., U.S.A.

As shown in FIGS. 1 and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered graphic 60. In this design, the registered graphic 60 includes simulated waist ruffles 62, simulated leg ruffles 64, a rainbow, sun, clouds, wagon and balloon. Again, any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/ polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 3) is positioned between the outer cover 40 and the bodyside liner 42, which components can be joined together by any suitable means such as adhesives as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 may suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent assembly 44 to better contain and absorb body exudates. The concentration of the superabsorbent particles may also vary through the thickness of the absorbent assembly 44. Alternatively, the absorbent assembly 44 may comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A. and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of fluff is identified with the trade designation CR1654, available from Kimberly-Clark Corporation, Neenah, Wis., U.S.A. and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that maintains the integrity and/or shape of absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of absorbent assembly. One suitable material is referred to as a surge layer (not shown) and comprises a material having a basis weight of about 50 grams per square meter, and comprising a through-air-bonded-carded web of a homogenous blend of 60 percent 3 denier bicomponent fiber comprising a polyester core/ polyethylene sheath, commercially available from BASF Corporation, and 40 percent 6 denier polyester fiber, commercially available from Hoechst Celanese Corporation, Portsmouth, Va., U.S.A.

As noted previously, the illustrated training pant 20 has a side panel 34 disposed on each side of the absorbent chassis 32. The pair of transversely opposed side panels 34 are permanently bonded to the composite structure 33 of the absorbent chassis 32 in at least one of the waist regions 22 and 24 and releasably attached to the absorbent chassis in the opposite waist region. For example, as shown best in FIGS. 2 and 3, the side panels 34 are permanently bonded to and extend transversely beyond the side edges 47 of the composite structure 33 in the back waist region 24 along an attachment line 66. It is desirable but not necessary for the absorbent chassis 32 to include side panels 34 that extend transversely outward from the composite structure.

The illustrated side panels 34 define a distal edge 68 spaced from the attachment line 66 and inner and outer edges 70 and 72 that extend from the side edges 36 of the absorbent chassis 32 to the distal edges. The inner edges 70 of the side panels 34 form part of the side edges 36 of the absorbent chassis 32 and are desirably angled relative to the transverse axis 49 to provide greater coverage toward the back of the pant as compared to the front of the pant. The outer edges 72 are desirably parallel to the transverse axis 49 and form part of the back waist edge 38 of the absorbent chassis 32. Further, the outer edges 72 are desirably substantially aligned with the linear end edges 45 of the composite structure 33, and particularly longitudinally offset by about 1 centimeter or less.

The side panels 34 are permanently bonded to the composite structure 33 along the attachment line 66 using attachment means known to those skilled in the art such as adhesive, thermal or ultrasonic bonding. In such a configuration, each of the side panels 34 can be releasably attached to the composite structure 33 in the front waist region 22 of the training pant 20 as will be discussed hereinafter in more detail. Alternatively, the side panels 34 may be permanently bonded to the side edges 47 in the front waist region 22 and releasably attached to the side edges 36 in the back waist region 24 if it is desired that the fasteners be located towards the back of the wearer. Such a configuration may be desirable to prevent a wearer from unfastening the article prematurely. Still alternatively, the training pant 20 can include side panels 34 extending transversely outward from the absorbent chassis 32 in each of the front and back waist regions 22 and 24. Then the side panels can releasably attach to one another or to portions of the training pant.

Each of the side panels 34 can include one or more individual, distinct pieces of material. In particular embodiments, for example, each side panel 34 can include front and back side panel portions that are joined at a seam (not shown). Still alternatively, each individual side panel 34 may include a single piece of material which is folded over upon itself along an intermediate fold line (not shown). And as noted above, both the front and back waist regions can include side panels (not shown).

The side panels 34 desirably comprise an elastic material capable of stretching in a direction parallel to the transverse axis 49 of the training pant 20. Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42.

The training pant 20 according to the present invention also includes a fastening system 80 for securing the training pant about the waist of the wearer (FIGS. 2 and 3). The illustrated fastening system 80 includes a pair of first fastening components 82 and 83 that are adapted to refastenably connect to a pair of second fastening components 84 and 85. In one embodiment, one surface of each of the first fastening components 82 and 83 comprises a plurality of engaging elements that project from that surface. The engaging elements of the first fastening components 82 and 83 are adapted to repeatedly engage and disengage the engaging elements of the second fastening components 84 and 85.

In one particular embodiment, the first fastening components 82 and 83 each comprise hook type fasteners and the second fastening components 84 and 85 each comprise complementary loop type fasteners. In another embodiment, the first fastening components 82 and 83 each comprise loop type fasteners and the second fastening components 84 and 85 each comprise complementary hook type fasteners. Loop type fasteners typically comprise a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material may be molded or extruded of nylon, polypropylene or another suitable material. Suitable single-sided hook materials for the first or second fastening components 82–85 are available from Velcro Industries B.V., Amsterdam, Netherlands or affiliates thereof, and are identified as Velcro HTH-829 with a unidirectional hook pattern and having a thickness of about 0.089 millimeters (3.5 mils) and HTH-851 with a unidirectional hook pattern and having a thickness of about 0.051 millimeters (2 mils).

With reference to the illustrated embodiment and in particular to FIG. 3, the first fastening components 82 and 83 are located on the inner surface 28 of the training pant 20 in the back waist region 24. The first fastening components 82 and 83 are desirably positioned along the distal edge 68 of the side panels 34. The first fastening components 82 and 83 can be adhered to the side panels 34 by any means known to those skilled in the art such as adhesive bonds, sonic bonds or thermal bonds.

With reference to FIG. 2, the second fastening components 84 and 85 are located on the outer surface 30 of the training pant 20 in the front waist region 22. The second fastening components 84 and 85 are sized to receive the first fastening components 82 and 83 and are desirably positioned along the side edges 36 of the absorbent chassis 32 abutting the front waist edge 38. The second fastening components 84 and 85 can be adhered to the outer cover 40 by any means known to those skilled in the art such as adhesive bonds, sonic bonds or thermal bonds. In an alternative embodiment, the training pant 20 includes only a single second fastening component disposed in the front waist region 22 for refastenably connecting to the first fastening components 82 and 83 (not shown). In a further alternative embodiment, the outer cover 40 and/or bodyside liner 42 functions as a second fastening component in that it comprises a material that is releasably engageable with the first fastening components 82 and 83. In other alternative embodiments, the first fastening components are located on the outer surface and the second fastening components are located on the inner surface. The second fastening components 84 and 85 are desirably rectangular, although they may alternatively be square, round, oval, curved or otherwise nonrectangularly shaped.

When the first and second fastening components 82–85 are releasably engaged, the side edges 36 of the absorbent chassis 32 in the crotch region 26 define the leg openings 52, and the waist edges 38 of the absorbent chassis, including the outer edges 72 of the side panels, define the waist opening 50. When connected, the fastening components 82–85 form refastenable seams (FIG. 1) that are constructed to be flexible and comfortable.

Figure 4:
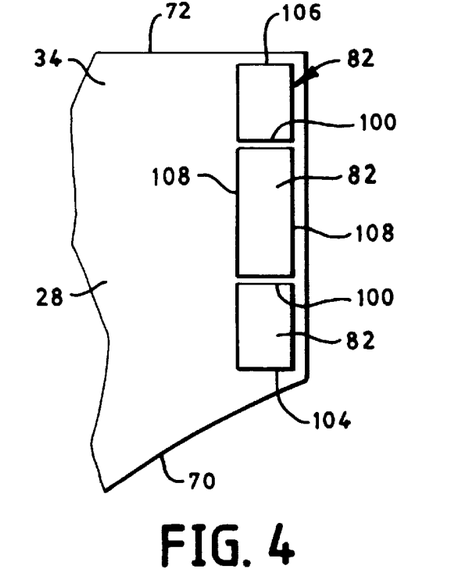
FIG. 4 illustrates an enlarged plan view of a side panel of the absorbent article shown in FIG. 1, and showing the surface of the article that faces the wearer when the article is worn.

FIG. 4 is an enlarged plan view of the inner surface 28 of one side panel 34 of the training pant 20. The illustrated first fastening component 82 comprises a pair of hinge areas 100 that transversely bisect the first fastening component. The first fastening component 82 defines an inner end edge 104 disposed toward the inner edge 70 of the side panel 34 and thus disposed toward one of the leg openings 52 when the fastening components are engaged, and an opposite outer end edge 106 disposed toward the outer edge 72 of the side panel and thus disposed toward the waist opening 50 when the fastening components are engaged. The first fastening component 82 also defines opposite side edges 108 that extend between the inner and outer end edges 104 and 106.

Figure 5:
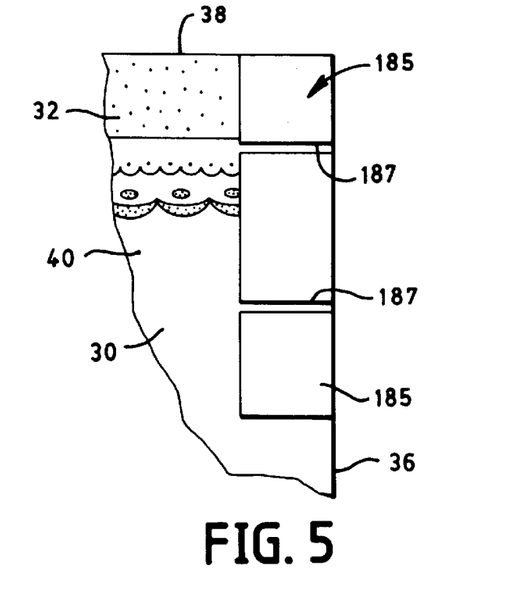
FIG. 5 illustrates an enlarged plan view of an alternative fastening component, and showing the surface of the article that faces away from the wearer when the article is worn.

An alternative second fastening component 185 is shown in FIG. 5. The second fastening component can be used on both sides of one waist region in combination with the first fastening components 82 and 83 illustrated in FIGS. 1, 3 and 4. The illustrated second fastening component 185 comprises a pair of hinge areas 187 that transversely bisect the fastening component. Thus, both the first and second fastening components 82–85 may comprise hinge areas.

Figure 6:
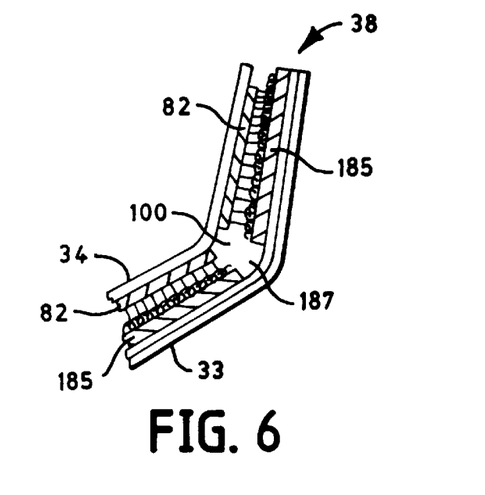
FIG. 6 schematically represents a section view through a refastenable seam formed by engagement of first and second fastening components according to one embodiment of the present invention.

As schematically illustrated in FIG. 6, which shows a section view through a refastenable seam formed by engagement of a first fastening component 83 and a second fastening component 185, the location of the hinge areas 100 on the first fastening components 82 and 83 can coincide with the location of the hinge areas 187 on the second fastening components 84 and 85. This alignment of the hinge areas form a freely flexing hinge.

Figure 7:
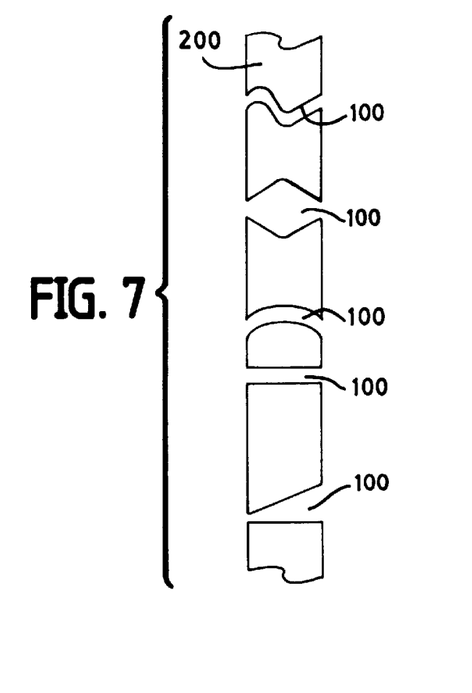
FIG. 7 illustrates a fastening component comprising a plurality of hinge areas.

Various configurations of hinge areas 100 in a fastening component 200 are illustrated in FIG. 7. The hinge areas 100 can comprise closely spaced mating shapes or different shapes. The fastening component comprises a plurality of individual segments that jointly define the length dimension, width dimension and length-to-width ratio of the fastening component. As illustrated in FIG. 7, the individual segments of the fastening component are desirably axially aligned with one another and aligned generally parallel to the longitudinal axis 48 of the training pant 20.

In particular embodiments, each of the first fastening components 82 and 83 and the second fastening components 84 and 85 defines a length dimension that is aligned generally parallel with the longitudinal axis 48 of the training pant 20 and a width dimension that is aligned generally parallel with the transverse axis 49 of the training pant. For a child of about 9 to about 15 kilograms (20–30 pounds, for example, the length dimension of the fastening components is desirably from about 5 to about 13 centimeters, such as about 10 centimeters, and the width dimension is desirably from about 0.5 to about 3 centimeters, such as about 2 centimeters. The fastening components desirably have a length-to-width ratio of about 2 or greater, such as about 2 to about 25, and particularly about 5 or greater, such as about 5 to about 8. Alternatively, the fastening components and refastenable seams may be disposed at an angle relative to the longitudinal axis or be curved or otherwise non-linear.

The training pant 20 may further include releasable side bonds (not shown) for improved reliability of maintaining the pant in a prefastened condition particularly when it is being pulled on or off over the hips of the wearer. Such releasable side bonds are desirably configured to be readily broken such that the caregiver can easily remove the training pant 20 after it has been soiled. The releasable side bonds desirably comprise ultrasonic point bonds. Absorbent articles including such releasable side bonds are further described in U.S. patent application entitled "Disposable Absorbent Articles Having Passive Side Bonds And Adjustable Fastening Systems" filed in the name of Elsberg on Jun. 19, 1998 and assigned U.S. Ser. No. 09/100,574, the disclosure of which is hereby incorporated by reference.

The methods of the different aspects of the present invention are directed at reliably and consistently providing the refastenable training pant 20 as described herein and representatively illustrated in the Figures. The various components of the training pant 20 are integrally assembled together employing various types of suitable attachment means, such as adhesive, sonic and thermal bonds or combinations thereof.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent article defining a longitudinal axis and first and second longitudinally spaced waist regions, the absorbent article comprising an absorbent chassis and a fastening system, the fastening system comprising at least one first fastening component attached to the absorbent chassis and disposed in the first waist region and at least one second fastening component attached to the absorbent chassis and disposed in the second waist region, the first and second fastening components adapted to releasably engage one another, the first fastening component having a length-to-width ratio of about 2 or greater, and comprising at least one hinge area that transversely bisects the first fastening component, wherein the first fastening component comprises a base layer and engaging elements projecting from the base layer, and the hinge area comprises a relatively Thin region of the base layer, wherein the hinge area extends the entire transverse width of the first fastening component.

2. The absorbent article of claim 1, wherein the relatively thin region is formed by melting with ultrasonics.

3. An absorbent article defining a longitudinal axis and first and second longitudinally spaced waist regions, the absorbent article comprising an absorbent chassis and a fastening system, the fastening system comprising at least one first fastening component attached to the absorbent chassis and disposed in the first waist region and at least one second fastening component attached to the absorbent chassis and disposed in the second waist region, the first and second fastening components adapted to releasably engage one another, the first fastening component having a length-to-width ratio of about 2 or greater, and comprising at least one hinge area that transversely bisects the first fastening component, wherein the first fastening component comprises a plurality of hinge areas spaced along the length of the fastening component, wherein the first fastening component comprises a base layer and engaging elements projecting from the base layer, and the hinge areas comprise relatively thin regions of the base layer, wherein the hinge areas e end the entire transverse width of the first fastening component.

4. The absorbent article of claim 3, wherein the relatively thin regions are formed by melting with ultrasonics.

5. An absorbent article defining a longitudinal axis, first and second longitudinally spaced waist regions, and a crotch region which extends between and interconnects the first and second waist regions, the absorbent article comprising an absorbent chassis and a fastening system, the fastening system comprising a pair of first fastening components attached to the absorbent chassis and disposed in the first waist region and at least one second fastening component attached to the absorbent chassis and disposed in the second waist region, the first and second fastening components comprising mechanical fastening elements that are adapted to releasably engage one another, each first fastening component having a length dimension, a width dimension, a length-to-width ratio of about 2 or greater, and at least one hinge area that transversely bisects the first fastening component, wherein each first fastening component comprises a base layer and engaging elements projecting from the base layer, and each hinge area comprises a relatively thin region of the base layer, wherein each hinge area extends the entire transverse width of the first fastening component.

6. The absorbent article of claim 5, wherein the relatively thin regions are formed by melting with ultrasonics.

7. An absorbent article defining a longitudinal axis, first and second longitudinally spaced waist regions, and a crotch region which extends between and interconnects the first and second waist regions, the absorbent article comprising an absorbent chassis and a fastening system, the fastening system comprising a pair of first fastening components attached to the absorbent chassis and disposed in the first waist region and at least one second fastening component attached to the absorbent chassis and disposed in the second waist region, the first and second fastening components comprising mechanical fastening elements that are adapted to releasably engage one another, each first fastening component having a length dimension, a width dimension, a length-to-width ratio of about 2 or greater, and at least one hinge area that transversely bisects the first fastening component, wherein each first fastening component comprises a plurality of hinge areas spaced along the length of the fastening component, wherein each first fastening component comprises a base layer and engaging elements projecting from the base layer, and the hinge areas comprise relatively thin regions of the base layer, wherein the hinge areas extend the entire transverse width of each first fastening component.

8. The absorbent article of claim 7, wherein the relatively thin regions are formed by melting with ultrasonics.

* * * * *